(12) United States Patent
Tsypko

(10) Patent No.: US 7,856,874 B2
(45) Date of Patent: Dec. 28, 2010

(54) APPARATUS AND METHOD FOR MEASURING A FLUID FLOW-RATE WITHIN A CAPILLARY

(75) Inventor: Nikolay Tsypko, Upper Nazareth (IL)

(73) Assignee: G.R.T. Development Ltd., Ramat Gan (IL)

( * ) Notice: Subject to any disclaimer, the term of this patent is extended or adjusted under 35 U.S.C. 154(b) by 16 days.

(21) Appl. No.: 12/092,387

(22) PCT Filed: Oct. 26, 2006

(86) PCT No.: PCT/IL2006/001232

§ 371 (c)(1), (2), (4) Date: Feb. 10, 2009

(87) PCT Pub. No.: WO2007/052253

PCT Pub. Date: May 10, 2007

(65) Prior Publication Data

US 2009/0235735 A1    Sep. 24, 2009

(30) Foreign Application Priority Data

Nov. 3, 2005    (IL) .................................... 171764

(51) Int. Cl.
*G01F 1/68* (2006.01)
(52) U.S. Cl. .................................................. 73/204.13
(58) Field of Classification Search ............... 73/204.13, 73/204.24; 417/415; 210/511; 165/185; 607/106; 62/3.2; 361/700
See application file for complete search history.

(56) References Cited

U.S. PATENT DOCUMENTS

| | | | |
|---|---|---|---|
| 4,753,111 A | 6/1988 | Caron et al. | |
| 4,947,889 A | 8/1990 | Ishikawa et al. | |
| 5,237,866 A | 8/1993 | Nijdam | |
| 5,755,559 A * | 5/1998 | Allington et al. ............... | 417/53 |
| 5,931,000 A * | 8/1999 | Turner et al. ................. | 62/3.2 |
| 6,386,050 B1 | 5/2002 | Yin | |
| 6,443,003 B1 | 9/2002 | Bailis | |
| 6,474,074 B2 * | 11/2002 | Ghoshal ........................ | 62/3.7 |

(Continued)

FOREIGN PATENT DOCUMENTS

DE    10063998    7/2001

(Continued)

OTHER PUBLICATIONS

International Search Report published Jun. 28, 2007 for PCT/IL2006/001232 filed Oct. 26, 2006.

(Continued)

*Primary Examiner*—Jewel Thompson
(74) *Attorney, Agent, or Firm*—Martin Fleit; Paul D. Bianco; Fleit Gibbons Gutman Bongini & Bianco PL

(57) ABSTRACT

An apparatus for measuring a fluid microflow velocity within a capillary conduit, comprises: a) at least one thermoelectric cooler having a heating and a cooling surface, said heating surface being suitable for heating a fluid flowing over it and said cooling surface being suitable for cooling said fluid; and b) a capillary conduit through which said fluid flows, said capillary conduit passing through said at least one thermoelectric cooler in heat-exchanging positioned relationship with its heating and cooling surfaces.

26 Claims, 12 Drawing Sheets

U.S. PATENT DOCUMENTS

| | | | |
|---|---|---|---|
| 7,082,031 B2 * | 7/2006 | Leija et al. | 361/700 |
| 7,127,954 B2 | 10/2006 | Markus | |
| 2003/0192595 A1 * | 10/2003 | Benson | 137/488 |
| 2004/0008335 A1 | 1/2004 | Hayes et al. | |
| 2004/0078028 A1 * | 4/2004 | Flaherty et al. | 604/892.1 |
| 2005/0223793 A1 | 10/2005 | Markus | |

FOREIGN PATENT DOCUMENTS

| | | |
|---|---|---|
| DE | 10221548 | 11/2003 |
| EP | 1586871 | 10/2005 |
| JP | 2004279377 | 10/2004 |

OTHER PUBLICATIONS

International Preliminary Report on Patentability published May 3, 2008 for PCT/IL2006/001232 filed Oct. 26, 2006.

Written Opinion published May 3, 2008 for PCT/IL2006/001232 filed Oct. 26, 2006.

* cited by examiner

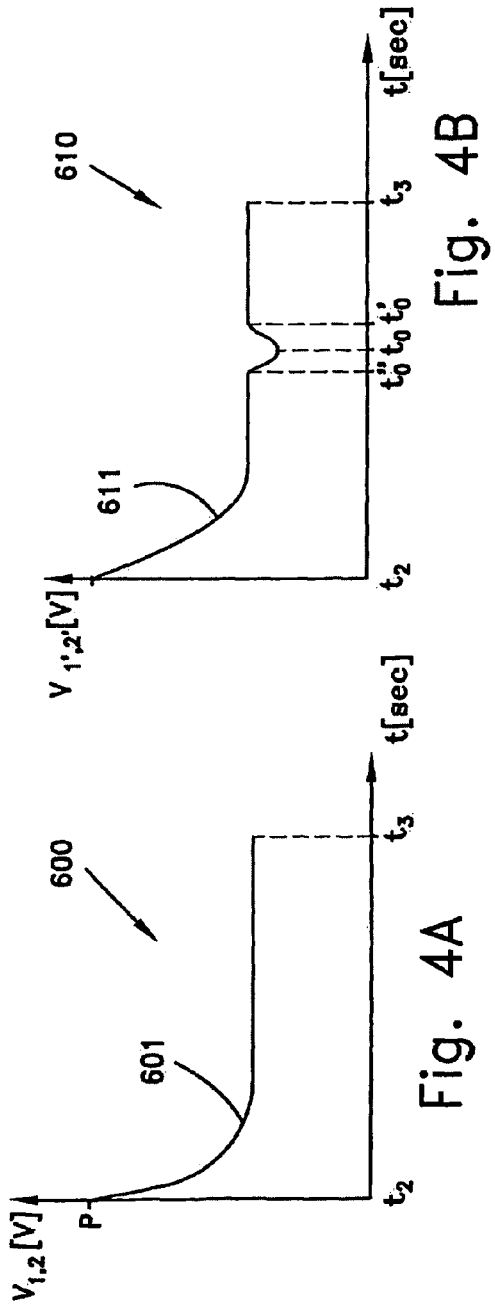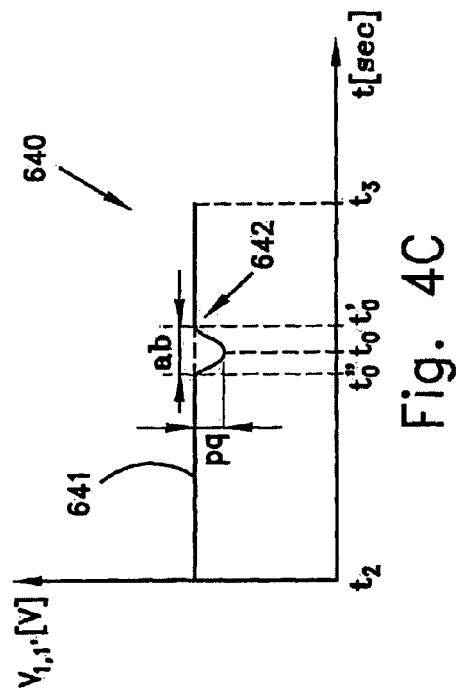

APPARATUS AND METHOD FOR MEASURING A FLUID FLOW-RATE WITHIN A CAPILLARY

FIELD OF THE INVENTION

The present invention relates to the field of flow measurement of gases and liquids. More particularly, the invention relates to a device and a method for measuring, with high precision, the flow of a fluid passing through it, even when the flow-rate of said fluid is very low, e.g. of the order of milliliters per hour or less.

DEFINITIONS, ACRONYMS AND ABBREVIATIONS

Throughout this specification, the following definition is employed:

Thermoelectric cooler: is a solid-state heat "pump" used in applications where temperature stabilization, temperature cycling, or cooling below ambient is required. There are many products using thermoelectric coolers, including cameras, laser diodes, microprocessors, blood analyzers and portable picnic coolers. Thermoelectric cooling uses the Peltier effect to create a heat flux between the junction of two different types of materials. There are no moving parts and such a device is maintenance free. The effect is also used in satellites and spacecraft to counter the effect of direct sunlight on one side of a craft whilst dissipating heat to the cold shaded side.

BACKGROUND OF THE INVENTION

There are various applications, which require a precise measurement of liquid or gas flow-rates (liquids and gases being hereinafter referred to collectively as "a fluid". Such precise measurements are particularly required in medical, process monitoring and control applications. Historically, a number of approaches have been developed, involving mechanical, electromagnetic and thermal techniques.

For example, U.S. Pat. No. 6,443,003 discloses a sensor for measuring changes in mass air flow by using one or more thermoelectric devices, each of which serves both as a heating element and as a differential temperature sensor. The thermoelectric device or devices are sandwiched between two surface plates. The sensor operates the device or devices in constant current or in pulsed current mode. The operation in constant current mode involves passing the current through one thermoelectric device to create a temperature differential between the two surfaces. A second thermoelectric device generates a voltage in response to the differential, the voltage being proportional to the air flow-rate.

U.S. Pat. No. 5,237,866 discloses an apparatus for measuring the flow of fluid comprising a tube through which the fluid to be measured may flow, including means for varying the temperature at a selected location on the tube. A plurality of temperature sensors are used to measure the temperature at upstream locations, and at least one sensor is used for measuring the temperature downstream of the selected location. A plurality of separate sensors are used on the input end to provide information to determine the temperature gradient along the tube.

U.S. Pat. No. 4,947,889 describes an apparatus in which a part of a tube, through which a fluid passes, is cooled by means of an electronic cooling element and a flow rate of the fluid is measured based on a temperature of a surface of the cooled tube.

U.S. Pat. No. 4,753,111 discloses a fluid flow meter using a pair of temperature-variable resistance elements as detectors. Both elements are exposed to the fluid flow and supplied with a series of current pulses. The pulses supplied to one element, the reference element, are of very short duration so, that there is no appreciable heating effect; the pulses supplied to the other element are of longer duration and are controlled so as to maintain this element at a fixed temperature differential above the other element, which remains at fluid temperature. The pulse width of the longer duration pulses is a measure of the flow rate of the fluid.

In spite of all efforts, the art has so far failed to provide a fluid flow-meter of simple configuration, which can be used to measure very low fluid flow-rates (also referred to hereinafter as "fluid microflow") and which is relatively inexpensive.

It is an object of the present invention to provide such a fluid flow-meter for measuring very low fluid flow rates (referred to hereinafter also as "microflowmeter") suitable for measuring, for instance, the velocity of fluid microflow within a narrow pipe, such as a capillary conduit, a vessel, etc.

It is another object of the present invention to provide a microflowmeter, which can also be used to determine whether components of a fluid, flowing within a narrow conduit, such as a capillary conduit, remain constant.

It is still another object of the present invention to provide a precise method and system for measuring fluid microflow within the narrow tube.

It is a further object of the present invention to provide a method and system, which is relatively inexpensive.

Other objects and advantages of the invention will become apparent as the description proceeds.

As used herein, the term "microflow" indicates the flow of a fluid having a flow rate of the order of magnitude of milliliters per hour or less. However, it should be appreciated that the ability to measure very small flaw rates does not deter in any way from the ability to measure greater flow-rates, and the measurement of such greater flow rates is within the scope of the invention.

SUMMARY OF THE INVENTION

The present invention relates to a method and to a microflowmeter device for measuring the fluid microflow within a narrow conduit, such as a capillary tube. According to a preferred embodiment, the invention further relates to a method and apparatus for determining whether the composition of the fluid remains constant.

The apparatus for measuring a fluid microflow velocity according to the invention comprises: (a) at least one thermoelectric cooler having a heating and a cooling surface, said heating surface being used for heating a fluid flowing over it and said cooling surface being used for cooling said fluid; and (b) a capillary conduit, preferably a tube, through which said fluid flows, said capillary conduit passing through said at least one thermoelectric cooler. The capillary tube is preferably in heat-exchanging positioned relationship with its heating and cooling surfaces.

According to a preferred embodiment of the invention, the apparatus further comprises an additional thermoelectric cooler connected to the first thermoelectric cooler or located at a predetermined distance therefrom.

According to another preferred embodiment of the invention, the apparatus further comprises at least one heat-transfer surface having a larger surface area than a heating or cooling surface area of the thermoelectric cooler, said heat-transfer surface operating as a heat-transfer element between the heating or cooling surface and the capillary conduit.

In one preferred embodiment of the invention the apparatus further comprises: (a) a pulse generator for generating at least one current or voltage pulse and for providing said pulse to the electrical contacts of the at least one thermoelectric cooler; (b) a differentiator for differentiating a thermoelectric cooler output signal; (c) an analyzer for analyzing a signal outputted from said differentiator and for determining one or more time marks related to the fluid or gas temperature extremum, said extremum being created as a result of the corresponding current or voltage pulse provided by said pulse generator; (d) at least one timer which is activated at the time of providing to said at least one thermoelectric cooler each current or voltage pulse, and which is deactivated at the time of receiving the time mark; (e) a microprocessor for processing at least one time signal received from said at least one timer, and for determining a fluid microflow velocity; and (f) an indicator or monitor for displaying said determined fluid microflow velocity.

According to a preferred embodiment of the invention, the apparatus further comprises an amplifier for amplifying the thermoelectric cooler output signal.

According to another preferred embodiment of the invention the apparatus further comprises at least one diode for preventing the thermoelectric cooler output signal from being transferred back to the pulse generator or to the at least one timer, at a time period between each two current or voltage pulses.

According to still another preferred embodiment of the invention the apparatus further comprises a transistor for providing a magnitude of the thermoelectric cooler output signal to the microprocessor.

According to yet another preferred embodiment of the invention, the apparatus further comprises at least one analog-to-digital converter for converting at least one analog signal and for inputting a converted signal to at least one input of the microprocessor.

According to a preferred embodiment of the invention, the microprocessor is employed to determine whether one or more components of the fluid flowing in the capillary conduit remain constant or are changed.

In this specification the terms "fluid flow" and "fluid flow velocity" are used interchangeably. As will be apparent to the skilled person, the flow rate of a fluid flowing through a conduit of known diameter is directly related to the fluid velocity.

The method for measuring a fluid microflow velocity within a capillary conduit, comprises: (a) providing at least one thermoelectric cooler having heating and cooling surfaces, said heating surface being used for heating a fluid flowing over it and said cooling surface being used for cooling said fluid; (b) providing a capillary conduit, preferably a tube, through which said fluid flows, said capillary conduit passing through said at least one thermoelectric cooler; (c) generating at least one current or voltage pulse by means of a pulse generator and providing said pulse to an electrical contacts of said at least one thermoelectric cooler; (d) differentiating a thermoelectric cooler output signal by means of a differentiator; (e) analyzing by means of an analyzer a signal outputted from said differentiator and determining one or more time marks related to the fluid temperature extremum, said extremum being created as a result of the corresponding current or voltage pulse provided by said pulse generator; (f) providing at least one timer activated at the time of providing to said at least one thermoelectric cooler each current or voltage pulse, and deactivated at the time of receiving the time mark; (g) processing by means of a microprocessor at least one time signal received from said at least one timer, and determining by said microprocessor a fluid microflow velocity; and, optionally, (h) displaying said determined fluid microflow velocity on an indicator or monitor or using a value representative of said determined velocity as the input to another device.

According to a preferred embodiment of the invention, the method further comprises providing an additional thermoelectric cooler, connected to the first thermoelectric cooler or located at a predetermined distance from said first thermoelectric cooler.

According to another preferred embodiment of the invention, the method further comprises effecting heat-transfer to the capillary conduit by means of at least one heat-transfer surface having a larger surface area than heating or cooling surface area of the thermoelectric cooler.

According to a preferred embodiment of the invention, the method further comprises amplifying the thermoelectric cooler output signal by means of an amplifier.

According to another preferred embodiment of the invention, the method further comprises preventing, by means of at least one diode, the thermoelectric cooler output signal from being transferred back to the pulse generator or to the at least one timer, at a time period between each two current or voltage pulses.

According to still another preferred embodiment of the invention, the method further comprises providing to the microprocessor by means of a transistor a magnitude of the thermoelectric cooler output signal.

According to yet another preferred embodiment of the invention, the method further comprises converting, by means of at least one analog-to-digital converter, at least one analog signal and inputting a converted signal to at least one input of the microprocessor.

According to a further preferred embodiment of the invention, the method further comprises determining by means of the microprocessor whether one or more components of the fluid flowing in the capillary conduit remain constant or have changed.

The invention also encompasses the use of the device of the invention as a measuring and/or a controlling device in apparatus using fluid flow.

Illustrative and non-limiting examples of such apparatus include medical devices, such as medicine dosing apparatus. Illustrative examples of such medical apparatus include dosing pumps, such as insulin pumps, intravenous drug dosing devices, intraluminal dosage devices, such as may supply low-dosage drugs, e.g., to the heart or an arterial occlusion via a catheter, drug supplying devices for use in brain surgery, etc.

Non-medical devices can also incorporate the apparatus or the method of the inventions, such as dosing devices used in industry, aviation and space applications, etc. All such devices, inasmuch as comprise a device according to the invention or employ the method of the invention in any other way, also form a part of the present invention.

BRIEF DESCRIPTION OF THE DRAWINGS

In the drawings:

FIG. 4A is a schematic graph, representing an output voltage signal in the time domain starting from the corresponding time period $t_2$, or $t_4$, or $t_6$, said signal is outputted, according to a preferred embodiment of the present invention, from electrical contacts 2 and 1 of the thermoelectric cooler;

FIG. 4B is a schematic graph, representing an output voltage signal in the time domain starting from the corresponding time period $t_2$, or $t_4$, or $t_6$, said signal outputted from electrical contacts 2' and 1' of the thermoelectric cooler, according to a preferred embodiment of the present invention;

FIG. 4C is a schematic graph, representing an output voltage signal in the time domain starting from the corresponding time period $t_2$, or $t_4$, or $t_6$, said signal is outputted from electrical contacts 1 and 1' of the thermoelectric coolers, while the electrical contacts 2 and 2' are short-circuited, according to a preferred embodiment of the present invention;

DETAILED DESCRIPTION OF THE PREFERRED EMBODIMENTS

Hereinafter, when the term fluid flow/microflow velocity is mentioned, it should be understood that it refers to the average velocity $V_{AV}$ [cm/sec] (or $V_{AV}$ [mm/sec] and the like), which is determined as a ratio of a volumetric fluid value P[cm$^3$] (or P[mm$^3$] and the like), flowing through a cross-section S of a narrow conduit, such as a capillary tube during time t[sec] (or t[msec] and the like), to a value of the area of said cross-section S. The cross-section S is defined by:

$$S = \frac{\pi \cdot diam^2}{4} [cm^2],$$

wherein the variable "diam" is an internal diameter of said narrow conduit. Therefore, the fluid flow/microflow velocity is defined as follows:

$$V_{AV} = \frac{P}{S \cdot t} [cm/sec].$$

Also, it should be understood that the term fluid flow/microflow mass m' [g/sec] (or m' [mg/sec] and the like) refers to a mass M[g] of fluid components flowing through the cross-section S of the narrow conduit during time t[sec]. Therefore, the fluid flow/microflow mass is formulated as follows:

$$m' = \frac{M}{t} = \frac{\rho \cdot P}{t} = \rho \cdot V_{AV} \cdot S [\text{g/sec}],$$

wherein ρ [g/cm³] (or ρ [g/mm³] and the like) is a fluid density.

Figure 1A:
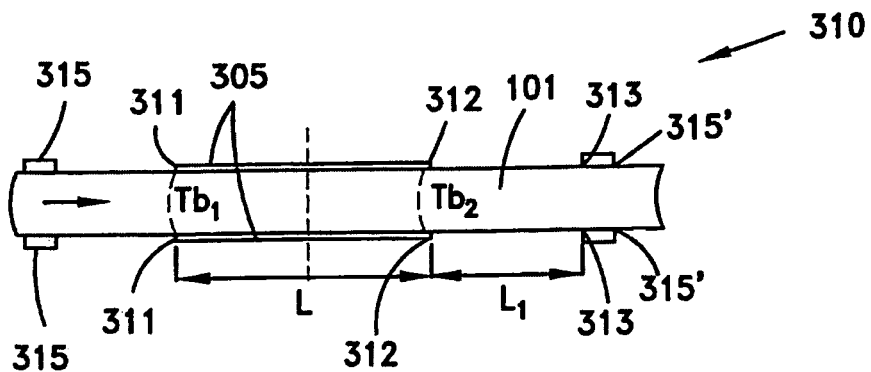
FIG. 1A is a schematic cross-sectional view of a device for measuring a fluid microflow within a narrow conduit, such as a capillary tube, according to the prior art.

FIG. 1A is a schematic cross-sectional view of a device 310 for measuring a fluid microflow within a narrow conduit, such as capillary tube 101, according to the prior art. Device 310 comprises a heating element 305 and first and second temperature sensors numbered 315 and 315', respectively. The temperature sensors 315 and 315' are positioned symmetrically from heating element 305. The fluid heating coefficient can be determined by obtaining the average fluid temperatures $Tb_1$ and $Tb_2$ within capillary tube 101. $Tb_1$ is the fluid temperature at entrance point 311 of the length L heated by heating element 305, and $Tb_2$ is the fluid temperature at exit point 312 of said length L.

Figure 1B:
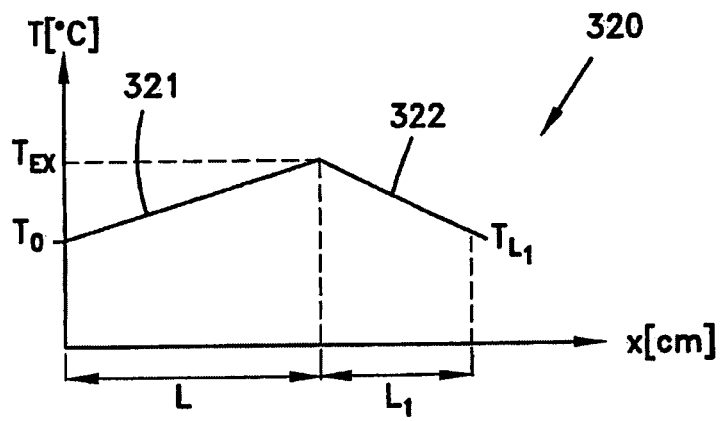
FIG. 1B is a schematic graph representing a temperature distribution along a capillary tube near a heating element, according to the prior art.

FIG. 1B is a schematic graph 320 representing a temperature distribution along capillary tube 101 (FIG. 1A) near heating element 305 (FIG. 1A), according to the prior art. $T_O$ is a capillary temperature at entrance point 311 (FIG. 1A) of the length L (FIG. 1A) heated by heating element 305; $T_{EX}$ is a capillary temperature at exit point 312 (FIG. 1A) of said length L; and $T_{L1}$ is a capillary temperature at point 313 (FIG. 1A). As is seen from graph 320, the temperature increases along the length L and decreases beyond it. The fluid microflow velocity within capillary tube 101 can be determined by analyzing the slopes of graph sections 321 and 322. The smaller the slope of section 321, the greater is the fluid microflow velocity.

It should be noted that it is assumed that the fluid within capillary tube 101 is flowing in the direction of temperature sensor 315'.

Figure 1C:
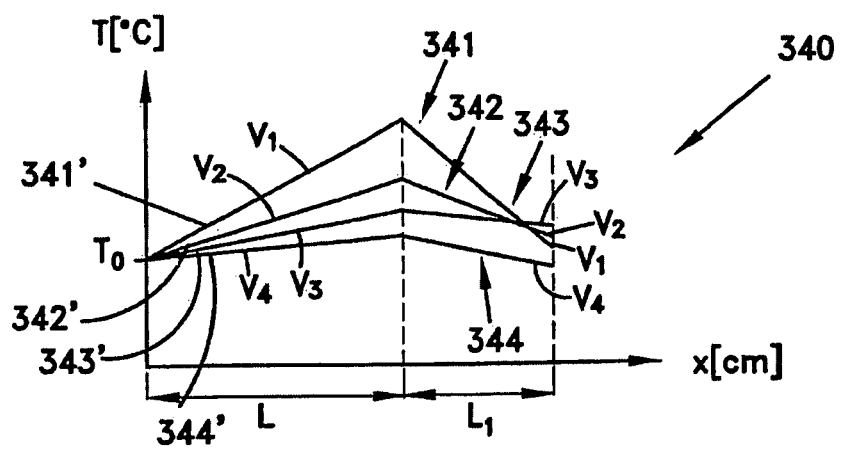
FIG. 1C is a schematic graph, representing a number of temperature distributions along a capillary tube near a heating element, said distributions relating respectively to different microflow velocities, according to the prior art.

FIG. 1C is a schematic graph 340, representing a number of temperature distributions 341, 342, 343 and 344 along capillary tube 101 (FIG. 1) near heating element 305 (FIG. 1A), said distributions relating respectively to different microflow velocities $V_1$, $V_2$, $V_3$ and $V_4$ ($V_1<V_2<V_3<V_4$), according to the prior art. Since $V_4$ is the largest microflow velocity, the fluid having such velocity and flowing along the length L (FIG. 1A), is heated relatively less, relative to the case in which said fluid has a smaller velocity, for example $V_2$. Therefore, section 344' has the smallest slope in comparison with other sections: 341', 342' and 343'. The smaller the slope of sections 341', 342', 343' and 344', the greater is the fluid microflow velocity. The accuracy of the prior art devices described in FIG. 1A to FIG. 1C significantly depends on the presence of a temperature gradient, besides the one created by heating element 305, said gradient existing in fluid flowing within capillary tube 101 (FIG. 1A). Furthermore, the prior art method according to FIG. 1A, FIG. 1B and FIG. 1C has a limited velocity measurement range, since it depends on the length $L_1$ (FIG. 1A); the smaller is $L_1$—the smaller is the dynamic fluid microflow velocity range. However, an increase in $L_1$ causes a decrease in fluid temperature at point 313, which in turn decreases the sensitivity to detect a change in the fluid microflow velocity.

The fluid flowing within capillary tube 101 (FIG. 1A) and having velocity $V_1$ takes more energy from heating element 305 (FIG. 1A) than the fluid flowing with velocity $V_2$, $V_3$, or $V_4$. The greater the fluid microflow velocity, the more energy it takes from heating element 305. Therefore, as a result, sections 341, 342, 343 and 344 can intersect each other at some distance after heating element 305.

Figure 1D:
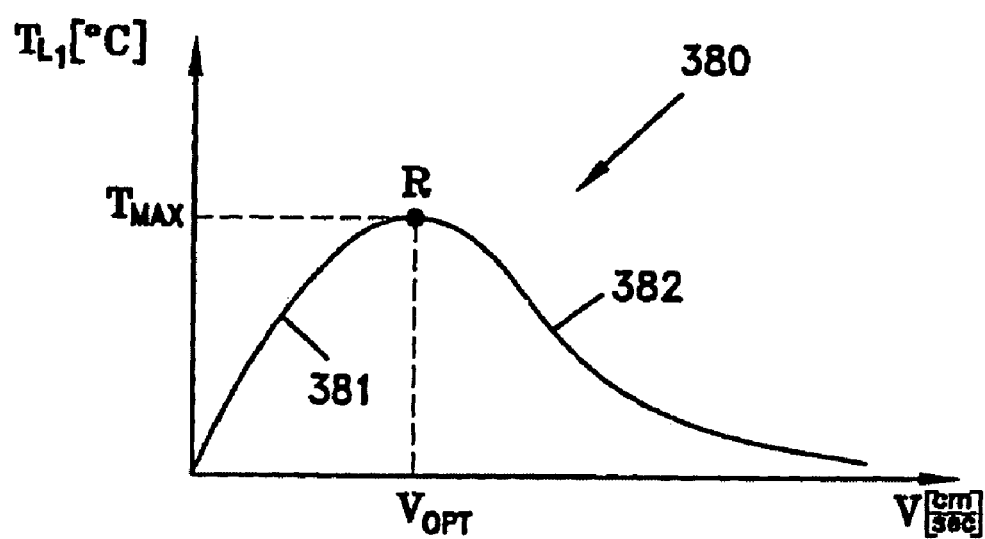
FIG. 1D is a schematic graph, representing a dependence of the fluid velocity on the capillary temperature, measured by temperature sensor, according to the prior art.

FIG. 1D is a schematic graph 380, representing a dependence of the fluid velocity V [cm/sec] on the capillary temperature $T_{L1}$ [° C.], measured by temperature sensor 315 (FIG. 1A), according to the prior art. The fluid temperature, and therefore the capillary temperature $T_{L1}$, gradually increases (at section 381) during heating, until it reaches its maximal value $T_{MAX}$. The $T_{MAX}$ temperature value relates to the optimal fluid velocity $V_{OPT}$. If the fluid velocity is greater than $V_{OPT}$, then $T_{L1}$ gradually decreases (at section 382). If the distance $L_1$ (FIG. 1A) between heating element 305 (FIG. 1A) and temperature sensor 315 decreases, then the dynamic range of measurements of the fluid microflow velocities within capillary tube 101 (FIG. 1A) also decreases. However, an increase of said distance $L_1$ causes a decrease in the sensitivity of detection of a fluid velocity change. A significant drawback of this prior art method is that only the fluid microflow velocities below or above $V_{OPT}$ can be determined, since it has to be known whether section 381 or 382 should be analyzed. Another drawback of this prior art method is that the fluid temperature gradient, besides the one caused by heating element 305, decreases the accuracy of the fluid microflow velocity measurements.

Figure 2:
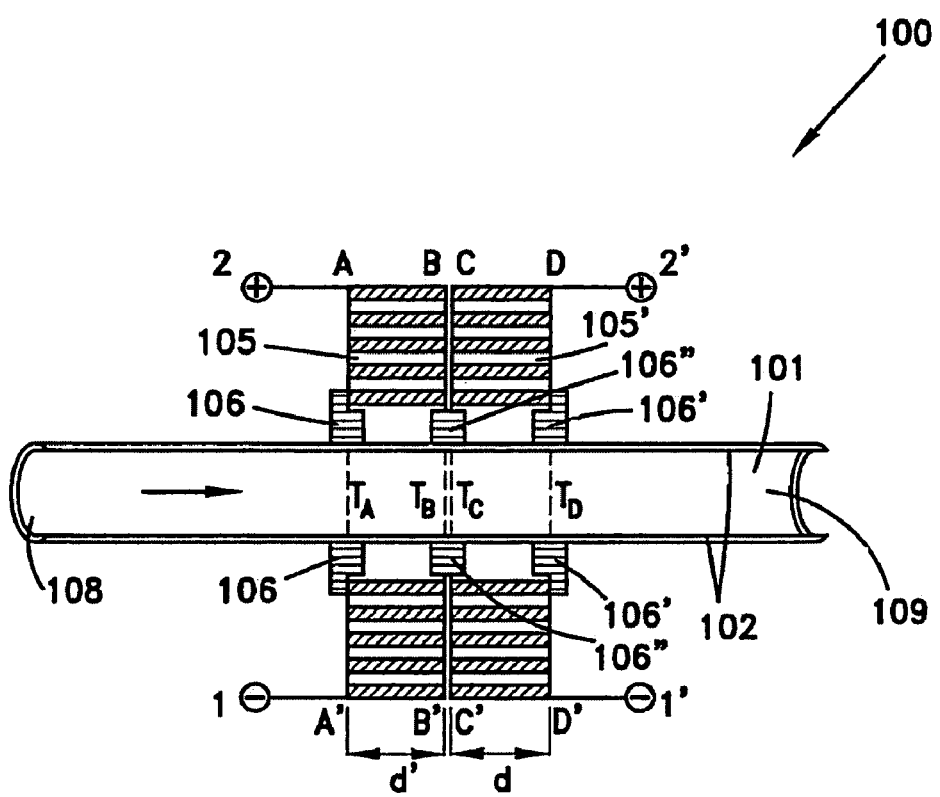
FIG. 2 is a schematic cross-sectional view of an apparatus for measuring a fluid or gas microflow within a narrow conduit, such as a capillary tube, comprising first and second thermoelectric coolers, according to a preferred embodiment of the present invention.

FIG. 2 is a schematic cross-sectional view of an apparatus 100 for measuring a fluid or gas microflow within a narrow conduit, such as capillary tube 101, comprising first and second thermoelectric coolers, 105 and 105', respectively, according to a preferred embodiment of the present invention. The thermoelectric coolers can be connected or attached to capillary tube 101 by means of heat-transfer surfaces 106, 106' and 106". Thermoelectric cooler 105 has a cooling surface AA' and a heating surface BB'. Similarly, thermoelectric cooler 105' has a cooling surface DD' and a heating surface CC'. Since these heating and cooling surfaces are usually thin, and each of them can have, for example a width of 0.8 mm, heat-transfer surfaces 106, 106' and 106" are used, which are wider than said heating and cooling surfaces, according to a preferred embodiment of the present invention. By use of heat-transfer surfaces 106, 106' and 106" the fluid flowing within capillary tube 101 is heated and/or cooled more efficiently, since the heat and/or cold provided by the thermoelectric coolers heating and cooling surfaces is spread on a larger area of capillary tube 101 (because the heat-transfer surfaces are wider than the heating and cooling surfaces). According to another preferred embodiment of the present invention, apparatus 100 does not comprise the above heat-transfer surfaces 106, 106' and 106".

It should be noted, that according to all preferred embodiments of the present invention, it is supposed that the fluid flowing within capillary tube 101 flows in the direction of the cooling surface DD'.

According to a preferred embodiment of the present invention, the heating surfaces BB' and CC' of thermoelectric coolers 105 and 105', respectively, are physically connected one to another or are located at a predetermined distance from one another. According to another preferred embodiment of the present invention, the cooling surfaces AA' and DD' of thermoelectric coolers 105 and 105', respectively, are physically connected one to another or are located at a predetermined distance from one another.

Generally, the direction of the current passing through electrical contacts 2, 2', 1 and 1' determines whether surfaces AA' and DD' are the cooling surfaces, and whether surfaces BB' and CC' are the heating surfaces. For example, suppose that the positive electrical contacts 2 and 2' are short-circuited and a series of positive input current or voltage pulses is supplied to said positive electrical contacts, then AA' and DD' will function as the cooling surfaces, and BB' and CC' will function as the heating surfaces. On the contrary, if a series of negative input current or voltage pulses is supplied to said positive electrical contacts, then AA' and DD' will function as the heating surfaces, and BB' and CC' will function as the cooling surfaces.

Within capillary 101 flows the fluid. Such fluid can be any suitable liquid, such as water, insulin, blood, etc., or a gas, such as methane, ammonia, etc. The direction of said fluid or gas microflow can be from the capillary tube proximate end 108, toward the capillary tube distal end 109, or vice versa.

The electrical current is supplied to thermoelectric coolers 105 and 105' through the thermoelectric coolers positive electrical contacts 2 and 2', and negative electrical contacts 1 and 1'. As a result, near the thermoelectric coolers heating and cooling surfaces there are created regions with increased and decreased fluid or gas temperature. According to a preferred embodiment of the present invention, the supplied electrical current is supplied in the form of pulses. The above regions with the increased and decreased fluid or gas temperature move in the direction of the fluid or gas microflow. As a result, the output voltage of the thermoelectric coolers electrical contacts 2 and 1, and 2' and 1' changes during the time intervals between each two supplied pulses. The fluid velocity is detected by measuring the duration of the time intervals between the peak voltage changes, said voltage being generated by thermoelectric coolers 105 and 105'. In order to determine whether the fluid density remains constant, the following parameters are analyzed: 1) the velocity of the fluid microflow; 2) the form and the value of the each peak voltage change; 3) $T_A$, $T_B$, $T_C$ and $T_D$, which are the temperatures of surfaces AA', BB', CC' and DD', respectively.

The thermoelectric coolers 105 and 105' can be of any suitable type and make. Such devices are commercially readily available. Examples of such commercial products are models "OT 1.2-62-F3" of the "Melcor® Corporation" located in the USA.

Figure 3A:
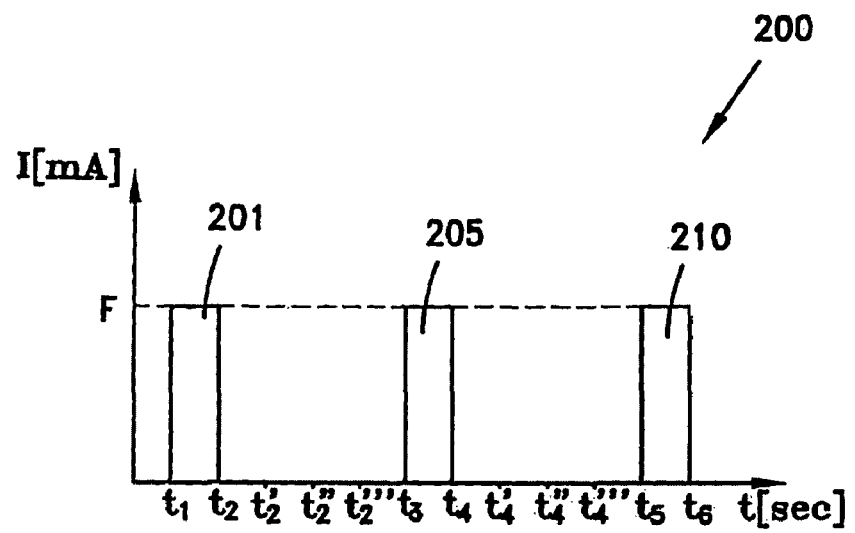
FIG. 3A is a schematic graph, representing a current input signal comprising a series of pulses, said signal being supplied to the thermoelectric coolers through their positive and negative electrical contacts, according to a preferred embodiment of the present invention.

FIG. 3A is a schematic graph 200, representing a current input signal comprising a series of pulses, said signal being supplied to thermoelectric coolers 105 and 105' through their positive electrical contacts 2 and 2', and negative electrical contacts 1 and 1', according to a preferred embodiment of the present invention. On the graph, the following parameters are denoted: F is a predetermined value of each pulse (F can be, for example 20 mA); $t_1$, $t_3$ and $t_5$ are the time periods, when the first, second and third pulses, respectively, are supplied; $t_2$, $t_4$ and $t_6$, are the time periods, when the first, second and third pulses, respectively, are terminated. Pulses 201, 205, 210 are supplied to thermoelectric coolers 105 and 105' through said thermoelectric coolers electrical positive and negative contacts: 2 and 2', and 1 and 1', respectively.

It should be noted, that in order to simplify the description of the present invention, all disclosed graphs comprise a limited number of signals, such as pulses, but this is done for the sake of brevity and clarity and it is not intended to limit the scope of the present invention in any way.

Figure 3B:
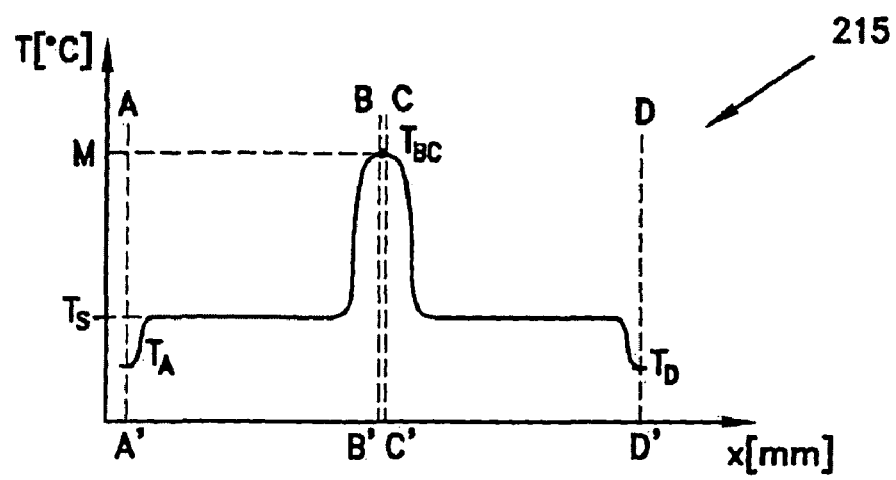
FIG. 3B is a schematic graph, showing the dependence of the fluid temperature on the distance, said temperature being measured on thermoelectric coolers cooling and heating surfaces, after supplying a pulse to the thermoelectric coolers electrical positive and negative contacts.

FIG. 3B is a schematic graph 215, showing the dependence of fluid temperature T on the distance X, said temperature being measured on thermoelectric coolers cooling and heating surfaces (FIG. 1): AA', DD' and BB', CC', respectively, after supplying a pulse to the thermoelectric coolers electrical positive and negative contacts.

Figure 3C:
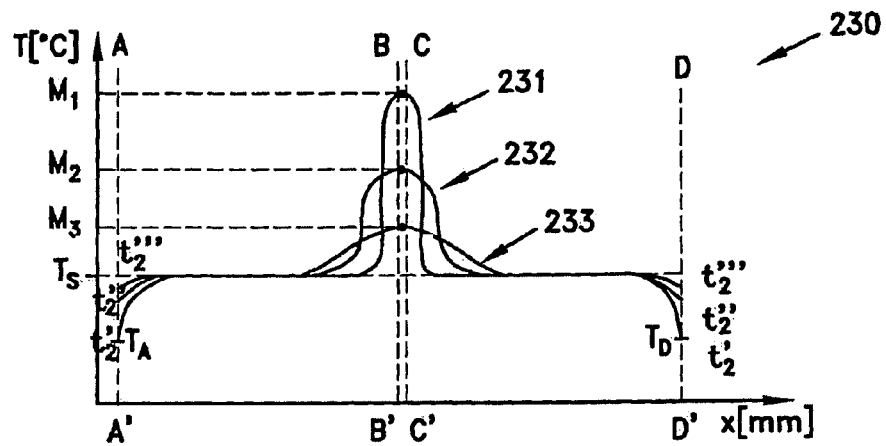
FIG. 3C is a schematic graph, showing the fluid temperature change in the time interval between time periods $t_2$ and $t_3$, according to a preferred embodiment of the present invention.

It should be noted, that in FIGS. 3B and 3C it is supposed, that the fluid in capillary tube 101 is not flowing.

The fluid temperature near the thermoelectric coolers heating surfaces BB' and CC' has the maximum value M, for example 2-3° C. above $T_S$ which is the temperature of the fluid if no series of pulses according to FIG. 3A are provided. The temperature gradually decreases toward the cooling surfaces AA' and DD'. At points $T_D$ and $T_A$ (the temperature of cooling surfaces DD' and AA', respectively) the temperature can be, for example 1° C. below $T_S$.

According to all preferred embodiments of the present invention, it is supposed that the temperature of capillary tube 101 and the temperature of the fluid at the corresponding point below said capillary tube 101 is equal. In addition, when a fluid temperature is mentioned, it refers to an average fluid temperature within capillary tube 101, unless otherwise stated. Furthermore, it is supposed that capillary tube 101 is relatively thin.

FIG. 3C is a schematic graph 230, showing the fluid temperature change in the time interval between time periods $t_2$ and $t_3$ (FIG. 3A), according to a preferred embodiment of the present invention. Curve 231 relates to time period $t_2'$ just after supplying pulse 201 (FIG. 3A). According to curve 231, the fluid temperature in the region of thermoelectric coolers heating surfaces BB' and CC' has maximum value $M_1$. $M_1$ can be, for example 2-3° C. above $T_S$, which is the temperature of the fluid if no series of pulses according to FIG. 3A is provided. Said fluid temperature decreases towards cooling surfaces AA' and DD' and reaches at points $T_D$ and $T_A$ on the surface of said cooling surfaces a value which can be, for example 1° C. below the $T_S$ value. Similarly, curves 232 and 233 relate to time periods $t_2''$ and $t_2'''$ (FIG. 3A), respectively. Maximum temperature value $M_2$ of curve 232 is smaller than $M_1$, since $t_2''$ is greater than $t_2'$, and the fluid within capillary tube 101 is cooled to some extent since pulse 201 termination at time $t_2$. Analogously, maximum temperature value $M_3$ of curve 233 is smaller than $M_2$. Therefore, the optimal time period for measuring the temperature difference $T_D$-$T_A$ (FIG. 1) is $t_2'$, when the maximum temperature value $M_1$ is the largest.

Figure 3D:
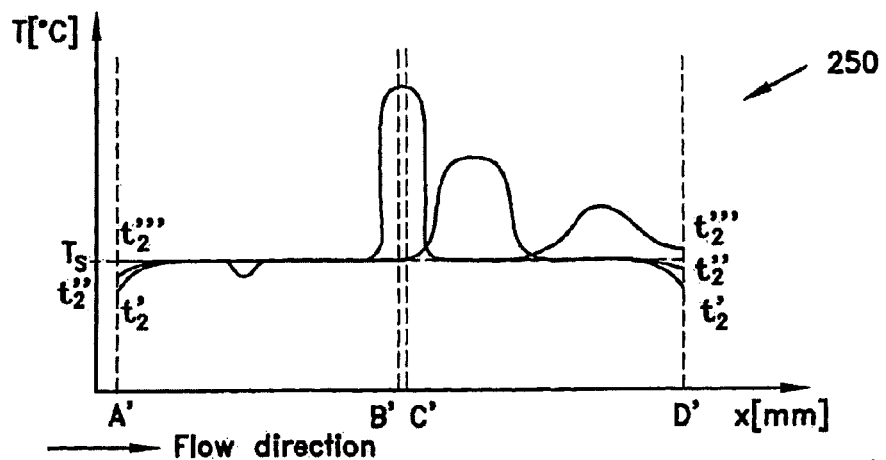
FIG. 3D is a schematic graph, showing a movement of the fluid temperature extremum within a capillary tube, according to a preferred embodiment of the present invention.

FIG. 3D is a schematic graph 250, showing a movement of the fluid temperature extremum within capillary tube 101, according to a preferred embodiment of the present invention. Because of the fluid microflow, curves 231, 232 and 233 (\FIG. 2C) are deformed and the maximum temperature values $M_1$, $M_2$ and $M_3$ are shifted in the direction of said microflow. The shifting distance of said maximum temperature values $M_1$, $M_2$ and $M_3$ is proportional to the fluid microflow velocity.

Figure 3E:
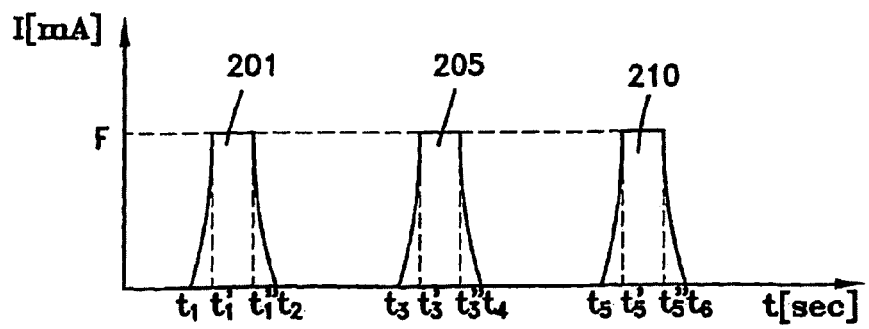
FIG. 3E is a schematic graph, representing a current input signal comprising a series of pulses, said signal being supplied, according to another preferred embodiment of the present invention, to the thermoelectric coolers through their positive and negative electrical contacts.

FIG. 3E is a schematic graph 280, representing a current input signal comprising a series of pulses, said signal being supplied, according to another preferred embodiment of the present invention, to thermoelectric coolers 105 and 105' through their positive electrical contacts 2 and 2', and negative electrical contacts 1 and 1'. During the first pulse 201, the current raises exponentially from $t_1$ to $t_1'$ until it reaches a predetermined value F, which can be, for example, 20 mA. Then after time $t_1''$, the current exponentially decreases until it becomes zero at time $t_2$. The second pulse 205, the third pulse 210 and the other following current pulses are provided in a similar way.

It should be noted that, according to another preferred embodiment of the present invention, instead of the current input signal comprising a series of pulses, a voltage input signal is provided, comprising a series of pulses.

FIG. 4A is a schematic graph 600, representing an output voltage signal 601 in the time domain starting from the corresponding time period $t_2$, or $t_4$, or $t_6$ (FIG. 3A), said signal is outputted, according to a preferred embodiment of the present invention, from electrical contacts 2 and 1 (FIG. 2) of thermoelectric cooler 105 (FIG. 2). As is shown on graph 600, after providing each current pulse 201, 205, and 210, the output voltage gradually decreases until the beginning of the next pulse. The faster a fluid flow within capillary tube 101, the larger is the slope of output voltage signal 601.

At the corresponding period of time $t_2$, or $t_4$, or $t_6$, thermoelectric cooler 105 starts operating as thermoelectric generator. The output voltage signal 601 is defined by the following expression:

$$V_{1,2} = \frac{1}{2} \cdot n \cdot (\alpha_1 - \alpha_2) \cdot (T_{BC} - T_A)$$

wherein $\alpha_1$ and $\alpha_2$ are coefficients characterizing an electromotive force ($\alpha_1$ or $\alpha_2$ can be, for example 400 µV/° C.); $T_{BC}$ is the difference of $T_B$ and $T_C$ ($T_{BC} = T_B - T_C$), which are the temperatures of the thermoelectric coolers heating surfaces BB' (FIG. 2) and CC' (FIG. 2), respectively; and $T_A$ is the temperature of the cooling surface AA' (FIG. 2) of thermoelectric cooler 105.

FIG. 4B is a schematic graph 610, representing an output voltage signal 611 in the time domain starting from the corresponding time period $t_2$, or $t_4$, or $t_6$ (FIG. 3A) According to a preferred embodiment of the present invention, said signal is outputted from electrical contacts 2' and 1' (FIG. 2) of thermoelectric cooler 105' (FIG. 2).

At the corresponding period of time $t_2$, or $t_4$, or $t_6$, thermoelectric cooler 105' similarly to thermoelectric cooler 105 starts operating as a thermoelectric generator. The output voltage signal 611 is defined by the following expression:

$$V_{1',2'} = \frac{1}{2} \cdot n \cdot (\alpha_1 - \alpha_2) \cdot (T_{BC} - T_D)$$

wherein $\alpha_1$ and $\alpha_2$ are coefficients characterizing an electromotive force ($\alpha_1$ or $\alpha_2$ can be, for example 400 µV/° C.); $T_{BC}$ is the difference of $T_B$ and $T_C$ ($T_{BC} = T_B - T_C$), which are the temperatures of the thermoelectric coolers heating surfaces BB' (FIG. 2) and CC' (FIG. 2), respectively; and $T_D$ is a temperature of the cooling surface DD' (FIG. 2) of thermoelectric cooler 105'.

FIG. 4C is a schematic graph 640, representing an output voltage signal 641 in the time domain starting from the corresponding time period $t_2$, or $t_4$, or $t_6$ (FIG. 3A). According to a preferred embodiment of the present invention said signal is outputted from electrical contacts 1 and 1' (FIG. 2) of thermoelectric coolers 105 and 105' (FIG. 2), respectively, while the electrical contacts 2 and 2' (FIG. 2) are short-circuited. The time $t_0$ relates to the period of time, when the fluid heated in the area BCC'B' (as shown on FIG. 2, said area is defined by thermoelectric coolers surfaces BB' and CC') during the corresponding pulse 201, 205 or 210 (FIG. 3A), arrives to the plain DD' (FIG. 2). The voltage value $V_{1,1'}$ of said output voltage signal 641 is mathematically determined by the following expression:

$$V_{1,1'} = \frac{1}{2} \cdot n \cdot (\alpha_1 - \alpha_2) \cdot (T_D - T_A)$$

(obtained by the difference of $V_{1,2}$ and $V_{1',2'}$), wherein n is a number of thermal elements within thermoelectric cooler 105 or 105' (it is supposed that both thermoelectric coolers are of the same type); $\alpha_1$ and $\alpha_2$ are coefficients characterizing an electromotive force ($\alpha_1$ or $\alpha_2$ can be, for example 400 µV/° C.); $T_D$ is a temperature of the cooling surface DD' of thermoelectric cooler 105'; and $T_A$ is a temperature of the cooling surface AA' (FIG. 2) of thermoelectric cooler 105. If there is no fluid flow within capillary tube 101 (FIG. 2), then $T_A$ is equal to $T_D$ during all time t, and therefore the output voltage signal 641 is zero during said all time t.

It should be noted, that the value of output voltage signal 641 does not depend on the fluid temperature distribution along the distance d (FIG. 2) between the thermoelectric coolers surfaces AA' and DD'. Also, the value of output voltage signal 641 at the corresponding time period $t_2$, or $t_4$, or $t_6$ (FIG. 3A) is denoted as $W_1$, which can be zero.

In addition, it should be noted that the value of output voltage signal 641 does not depend on thermo-physical properties of the material from which capillary tube 101 is made, and it does not depend on the thermo-physical properties of the fluid flowing within said capillary tube.

Furthermore, it is supposed that there is no temperature gradient in the fluid, besides that caused by thermoelectric coolers 105 and 105'. If a temperature gradient is present in the fluid, besides the one caused by thermoelectric coolers 105 and 105', then this gradient have to be taken into the account while calculating $V_{1,1'}$ and $V_{1,2}$, $V_{1',2'}$ (FIGS. 4A and 4B). However, it should be noted that, in general, the form of the output voltage signal 641 would remain the same.

If the time $t_0$ and the distance d (FIG. 2) are known, then the average velocity of the fluid or gas can be determined by the following equation:

$$V_{AV} = \frac{d}{t_0 - \tau_B}$$

wherein d is the width of thermoelectric cooler 105'; and $\tau_B$ is determined empirically by taking a number of experiments. $\tau_B$ depends on the transfer time-constant of thermoelectric cooler 105', on the heat (thermal) capacity of heat-transfer surfaces 106, 106', 106", and on the heat (thermal) capacity of wall 102 (FIG. 2) of capillary tube 101 (FIG. 2). The method for measuring the fluid velocity in capillary tube 101, according to a preferred embodiment of the present invention, does not depend on the fluid temperature change within said capillary tube 101, since the time to relates only to a local extremum 642 of the overall temperature distribution 641.

According to a preferred embodiment of the present invention, the coefficient $\tau_B$ is decreased by supplying a current input signal as illustrated in FIG. 3E, which comprises a series of pulses 201, 205, 210, etc., said signal being supplied to thermoelectric coolers 105 and 105' through their positive electrical contacts 2 and 2', and negative electrical contacts 1 and 1'.

It should be noted, that according to all embodiments of the present invention, distances d and d' (FIG. 2 and FIG. 5A) which are the width of thermoelectric coolers 105 and 105', respectively, comprise the width of the heating surfaces CC' and BB', and the width of the cooling surfaces DD', and AA', respectively.

Figure 4D:
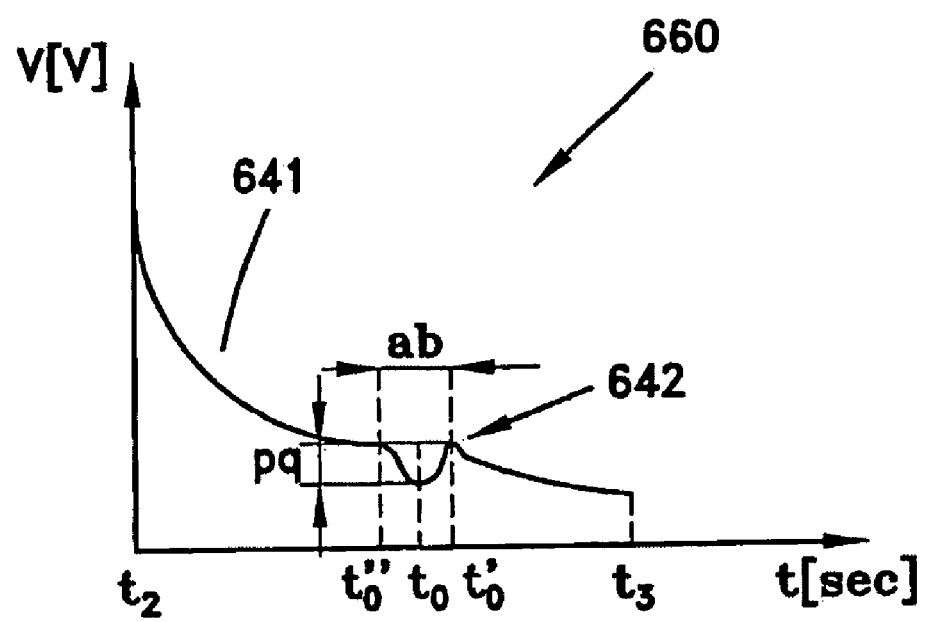
FIG. 4D is a schematic graph, representing an exemplary output voltage signal in the time domain starting from the corresponding time period $t_2$, or $t_4$, or $t_6$, said signal being outputted from electrical contacts 1 and 1' of the thermoelectric coolers, while the electrical contacts 2 and 2' are short-circuited, according to a preferred embodiment of the present invention.

FIG. 4D is a schematic graph 660, representing an exemplary output voltage signal 641 in the time domain starting from the corresponding time period $t_2$, or $t_4$, or $t_6$ (FIG. 3A), said signal being outputted from electrical contacts 1 and 1' (FIG. 2) of thermoelectric coolers 105 and 105' (FIG. 2), respectively, while the electrical contacts 2 and 2' (FIG. 2) are short-circuited, according to a preferred embodiment of the present invention. Similarly to FIG. 4C, the time $t_0$ relates to the period of time, when the fluid, heated in the area BCC'B'

(as shown on FIG. 2, said area is defined by thermoelectric coolers surfaces BB' and CC') during the pulse time period $t_2$-$t_1$ (FIG. 3A), arrives to the surfaces DD' (FIG. 2).

The time $t_0$ relates to a local extremum 642 of the overall distribution 641, and therefore $t_0$ does not depend on the fluid temperature change within capillary tube 101 (FIG. 2). For the same average fluid velocity and for the same physical conditions (such as the temperature gradient in the fluid, besides the one caused by the thermoelectric coolers) of apparatus 100 (FIG. 2), the greater the heat (thermal) conductivity K of heat-transfer surfaces 106, 106', 106" and of wall 102 (FIG. 2) of capillary tube 101, the greater is the length of the section ab. The smaller the result of the following expression $\rho \cdot c$ ($\rho$ is a fluid or gas density and c is a heat (thermal) capacity (measured in $$\frac{\text{Joule}}{\text{kg} \cdot {}^\circ \text{C.}}$$

units) of heat-transfer surfaces 106, 106', 106"), the greater is the length of the section pq. Therefore, the ratio $$\frac{ab}{PQ}$$

is proportional to $$\beta_o \cdot \frac{K}{\rho \cdot c} = \beta_o \cdot \alpha,$$

wherein $\alpha$ is a coefficient of temperature conductivity of the fluid; and $\beta_O$ is a proportionality coefficient depending on the fluid velocity in capillary tube 101. $\beta_O$ is defined empirically by taking a number of experiments with different fluid flow velocities. The result of the multiplication of ab·PQ actually defines the amount of energy "pumped" into the fluid. For the same type of fluid and for the same fluid flow velocity, the expression ab·PQ has a constant value. By taking a number of experiments with different types of fluids (or with different fluid ingredients) and with different fluid flow velocities, a look-up table for determining $$\frac{ab}{PQ}$$

value is obtained. As a result, the type of fluid (or ingredients of said fluid) can be determined and controlled. The value of ab can be, for example 0.5 or 5 seconds. The value of pq can be, for example 0.02V, 0.2V or 3V.

Figure 5A:
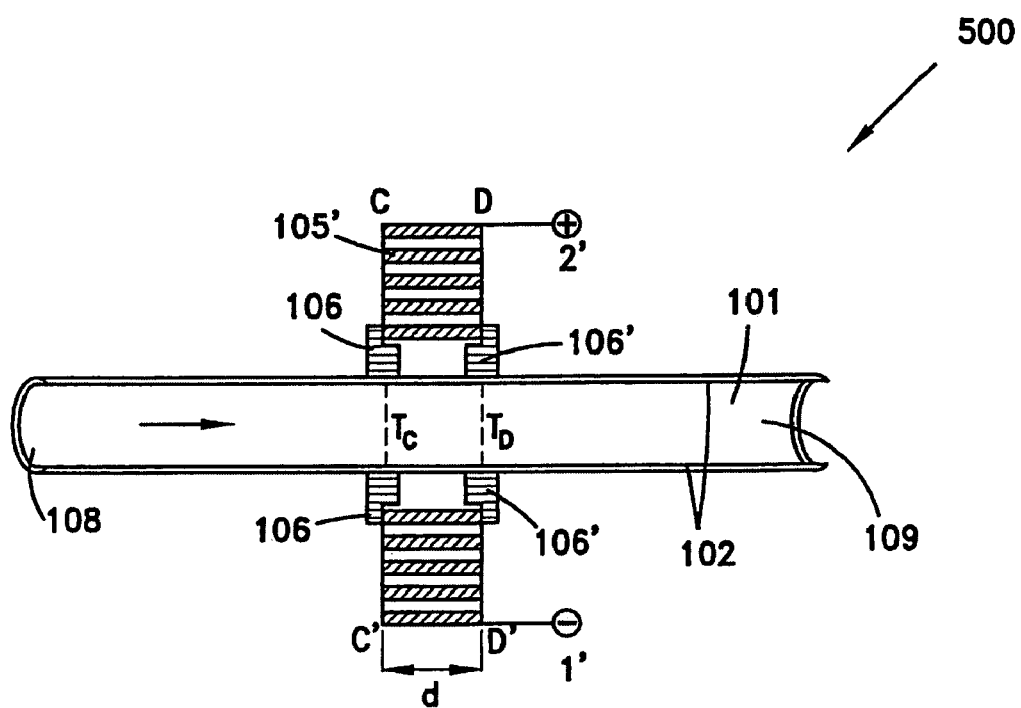
FIG. 5A is a schematic illustration of an apparatus for measuring a fluid flow within a narrow conduit, such as a capillary tube, according to another preferred embodiment of the present invention.

FIG. 5A is a schematic illustration of an apparatus 500 for measuring a fluid flow within a narrow conduit, such as capillary tube 101, according to another preferred embodiment of the present invention. Apparatus 500 comprises a single thermoelectric cooler 105' (having a cooling surface CC' and a heating surface DD') and capillary tube 101. When providing to thermoelectric cooler 105' by means of its positive and negative electronic contacts 2' and 1', respectively, a number of pulses (FIG. 3A), then the output voltage signal 611 in the time domain (FIG. 4B) is obtained, starting from the corresponding time period $t_2$, or $t_4$, or $t_6$ (FIG. 3A). The output voltage signal 611 is outputted from said electrical contacts 2' and 1' in the time interval between the pulses.

Since the heating and cooling surfaces CC' and DD' are usually thin and each of them can have, for example a width of 0.8 mm, according to a preferred embodiment of the present invention heat-transfer surfaces 106 and 106' are used, which are wider than said heating and cooling surfaces. By using heat-transfer surfaces 106 and 106', the fluid within capillary tube 101 is heated and/or cooled more efficiently, since the heat and/or cold provided by the thermoelectric coolers heating and cooling surfaces is spread over a larger area of capillary tube 101 (because the heat-transfer surfaces are wider than the heating and cooling surfaces). According to another preferred embodiment of the present invention, apparatus 500 does not comprise the above heat-transfer surfaces 106 and 106'.

Figure 5B:
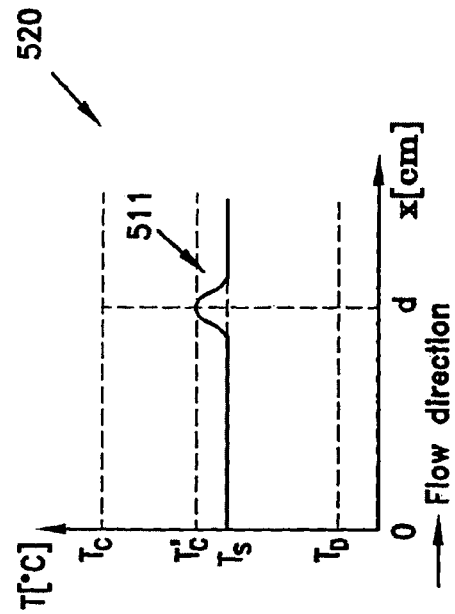
FIG. 5B is a schematic graph, representing a temperature distribution along the distance d at the time $t_0''$, according to a preferred embodiment of the present invention.

FIG. 5B is a schematic graph 510, representing a temperature distribution along the distance d (FIG. 5A) at the time $t_0'''$ (FIG. 4B), according to a preferred embodiment of the present invention. Temperature extremum 511 moves toward cooling surface DD' (FIG. 5A) located at the distance d from heating surface CC' (FIG. 5A). $T_D$ is the temperature of cooling surface DD' and $T_C$ is the temperature of heating surface CC'. $T_S$ is the temperature of the fluid within capillary tube 101 (FIG. 5A) if no current pulse, such as 201, 205 or 210 (FIG. 3A) is provided to electrical contacts 2' and 1' of thermoelectric cooler 105'.

Figure 5C:
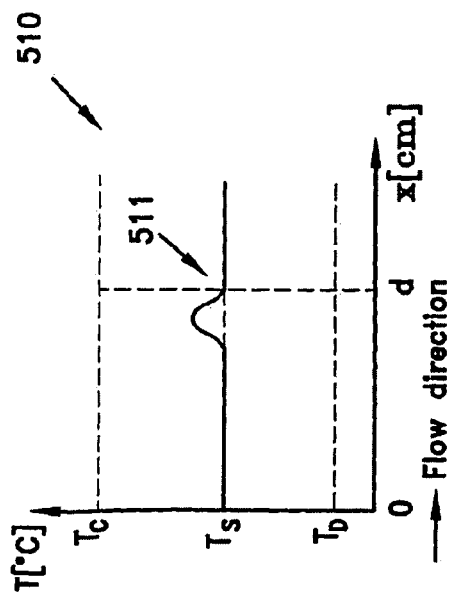
FIG. 5C is a schematic graph, representing a temperature distribution along the distance d at the time $t_0$, according to a preferred embodiment of the present invention.

FIG. 5C is a schematic graph 520, representing a temperature distribution along the distance d (FIG. 5A) at the time to (FIG. 4B), according to a preferred embodiment of the present invention. Temperature extremum 511 is located at the cooling surface DD'. $T'_C$ is a maximal temperature of extremum 511. $T'_C$ is detected at the time period $t_0$ at the distance d from heating surface CC'. $T_D$ is the temperature of cooling surface DD' and $T_C$ is the temperature of heating surface CC'. $T_S$ is the temperature of the fluid within capillary tube 101 (FIG. 5A) if no current pulse, such as 201, 205 or 210 (FIG. 3A) is provided to electrical contacts 2' and 1' of thermoelectric cooler 105'.

Figure 5D:
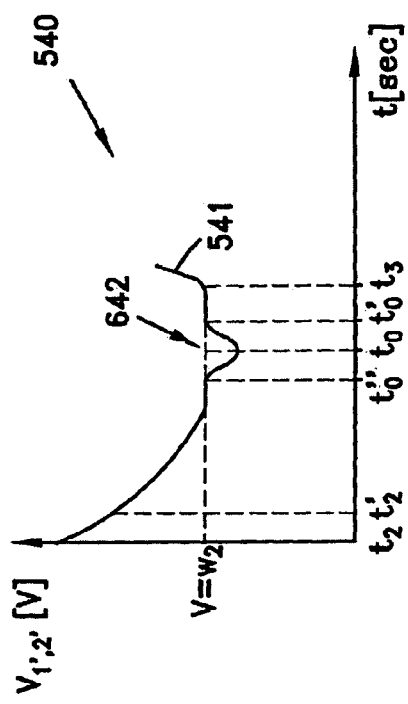
FIG. 5D is a schematic graph, representing an output voltage signal in the time domain starting from the corresponding time period $t_2$, or $t_4$, or $t_6$, said signal is outputted from electrical contacts 1' and 2' of the thermoelectric cooler, according to a preferred embodiment of the present invention.

FIG. 5D is a schematic graph 540, representing an output voltage signal 541 in the time domain starting from the corresponding time period $t_2$, or $t_4$, or $t_6$ (FIG. 3A), said signal is outputted from electrical contacts 1' and 2' (FIG. 5A) of thermoelectric cooler 105' (FIG. 5A), according to a preferred embodiment of the present invention.

The time $t_0$ relates to the period of time, when the fluid heated at the heating surface CC' (FIG. 5A) during the corresponding pulse 201, 205 or 210 (FIG. 3A), arrives to the surface DD' (FIG. 2). The voltage value $V_{1',2'}$ of said output voltage signal 541 is mathematically determined by the following expression:

$$V_{1',2'} = \frac{1}{2} \cdot n \cdot (\alpha_1 - \alpha_2) \cdot (T_S - T'_C)$$

wherein n is the number of thermal elements within thermoelectric cooler 105'; $\alpha_1$ and $\alpha_2$ are coefficients characterizing an electromotive force ($\alpha_1$ or $\alpha_2$ can be, for example 400 µV/° C.); $T'_C$ is a maximal temperature of extremum 642 (FIG. 5C); and $T_S$ is the temperature of the fluid or gas within capillary tube 101 (FIG. 5A) if no current pulse, such as 201, 205 or 210 is provided to electrical contacts 2' and 1' of thermoelectric cooler 105'. If there is no fluid flow within capillary tube 101 (FIG. 2), then $T_S$ is equal to $T_C'$ during all time t, and therefore the output voltage signal 541 is zero during said all time t.

It should be noted, that the value of output voltage signal 541 does not depend on the fluid temperature distribution along the distance d (FIG. 5A) between the thermoelectric coolers surfaces CC' and DD'.

In addition, it should be noted that the value of output voltage signal 541 does not depend on the thermo-physical properties of the material from which capillary tube 101 is made, and it does not depend on the thermo-physical properties of the fluid flowing within said capillary tube.

Furthermore, it is supposed that there is no temperature gradient in the fluid flow, besides that caused by thermoelectric cooler 105'. If said flow comprises a temperature gradient, beside the one caused by thermoelectric cooler 105', then this gradient has to be taken into account while calculating $V_{1',2'}$. However, it should be noted, that, in general, the form of the output voltage signal 541 would remain the same.

If the time $t_0$ and the distance d are known, then the average velocity of the fluid can be determined by the following equation:

$$V_{AV} = \frac{d}{t_0 - \tau_B}$$

wherein d is the width of thermoelectric cooler 105'; and $\tau_B$ is determined empirically by taking a number of experiments. $\tau_B$ depends on the transfer time-constant of thermoelectric cooler 105', on the heat (thermal) capacity of heat-transfer surfaces 106 and 106' and on the heat (thermal) capacity of wall 102 (FIG. 5A) of capillary tube 101. The method for measuring fluid or gas velocity in capillary tube 101, according to a preferred embodiment of the present invention, does not depend on the fluid temperature change within said capillary tube 101, since the time to relates only to a local extremum 642 of the overall temperature distribution 541.

Figure 5E:
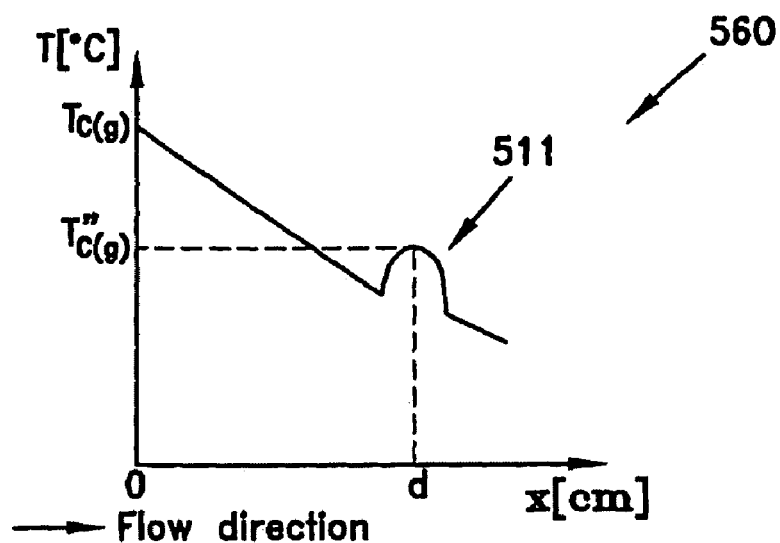
FIG. 5E is an exemplary schematic graph, representing a temperature distribution along the distance d at the time $t_0$ when there is a temperature gradient within the fluid flow, according to a preferred embodiment of the present invention.

FIG. 5E is an exemplary schematic graph 560, representing a temperature distribution along the distance d (FIG. 5A) at the time $t_0$ (FIG. 4B) when there is a temperature gradient within the fluid flow, according to a preferred embodiment of the present invention. $T_C(g)''$ is a maximal temperature of extremum 511 at time $t_0$.

Figure 5F:
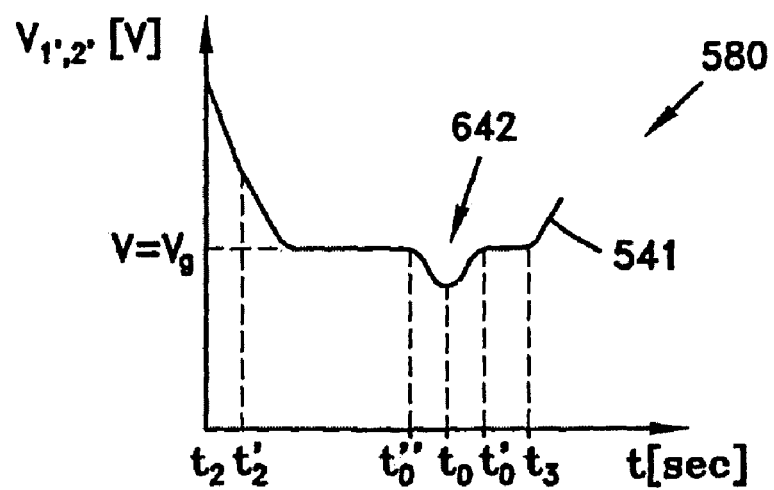
FIG. 5F is an exemplary schematic graph, representing an output voltage signal in the time domain starting from the corresponding time period $t_2$, or $t_4$, or $t_6$, said signal being outputted from electrical contacts 1' and 2' of the thermoelectric cooler when there is a temperature gradient within the fluid flow, according to a preferred embodiment of the present invention.

FIG. 5F is an exemplary schematic graph 580, representing an output voltage signal 541 in the time domain starting from the corresponding time period $t_2$, or $t_4$, or $t_6$ (FIG. 3A), said signal being outputted from electrical contacts 1' and 2' (FIG. 5A) of thermoelectric cooler 105' (FIG. 5A) when there is a temperature gradient within the fluid flow, according to a preferred embodiment of the present invention.

Figure 6A:
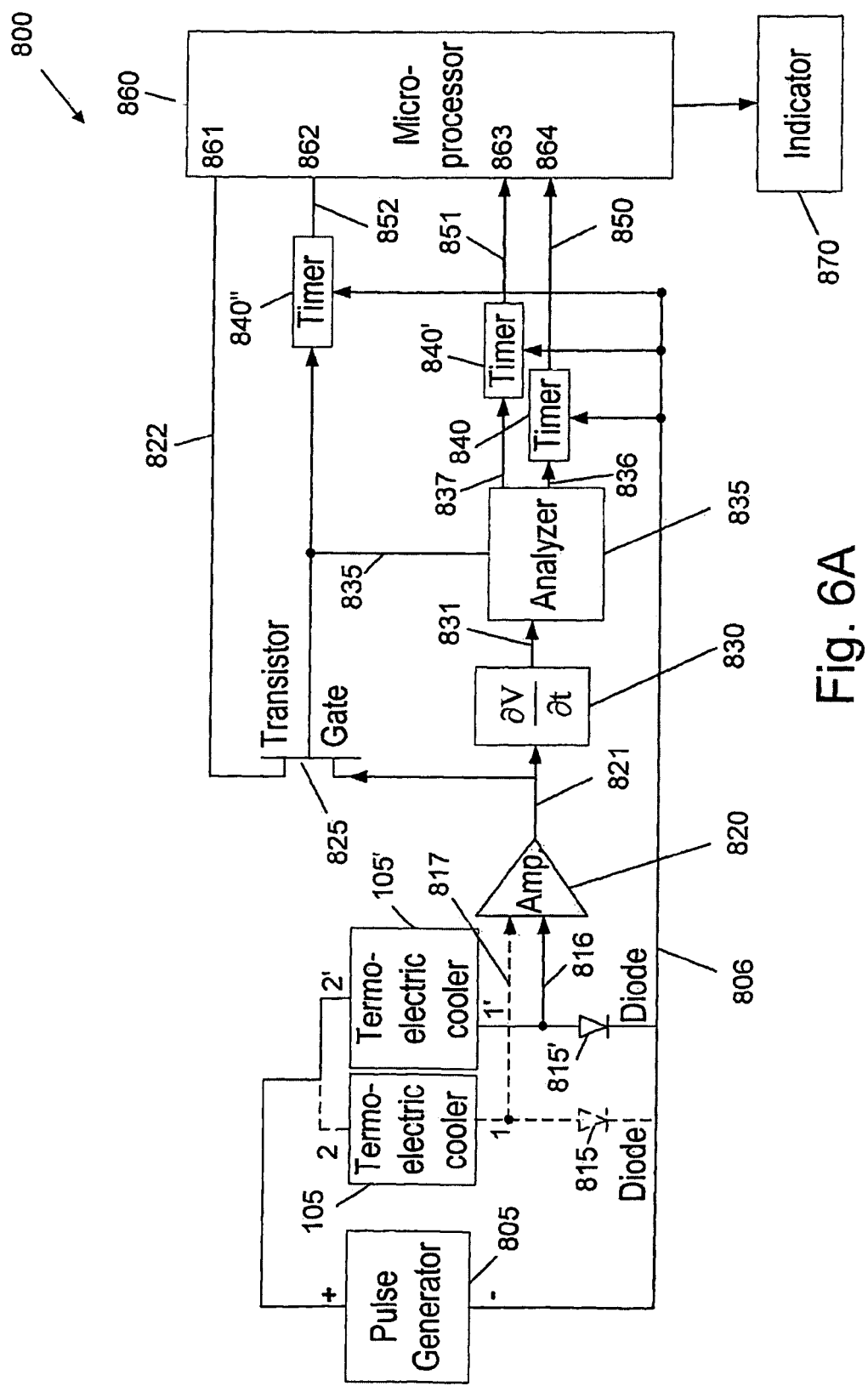
FIG. 6A is an exemplary electronic schematic block diagram scheme of a system utilizing an apparatus of the present invention, used for measuring a fluid flow within a narrow conduit, such as a capillary tube, according to a preferred embodiment of the present invention.

FIG. 6A is an exemplary electronic schematic block diagram scheme 800 of a system utilizing apparatus 100 or 500, used for measuring a fluid flow within a narrow conduit, such as capillary tube 101 (FIG. 2), according to a preferred embodiment of the present invention. The system comprises a pulse-generator 805, at least one thermoelectric cooler 105' (in addition, it can comprise a second cooler 105), at least one diode 815' (in addition, it can comprise an additional diode 815), an amplifier 820, a transistor 825, such as FET (Field Effect Transistor) or MOSFET (Metal-Oxide-Semiconductor Field-Effect Transistor), a differentiator 830, an analyzer 835, timers 840, 840' and 840", a microprocessor 860 and an indicator 870. It should be noted, that electronic schematic block-diagram scheme 800 can comprise a number of analog-to-digital converters (A/Ds) for converting analog signals and inputting them to inputs 861, 862, 863 and 864 of microprocessor 860, if said microprocessor does not comprise such A/Ds.

Figure 6B:
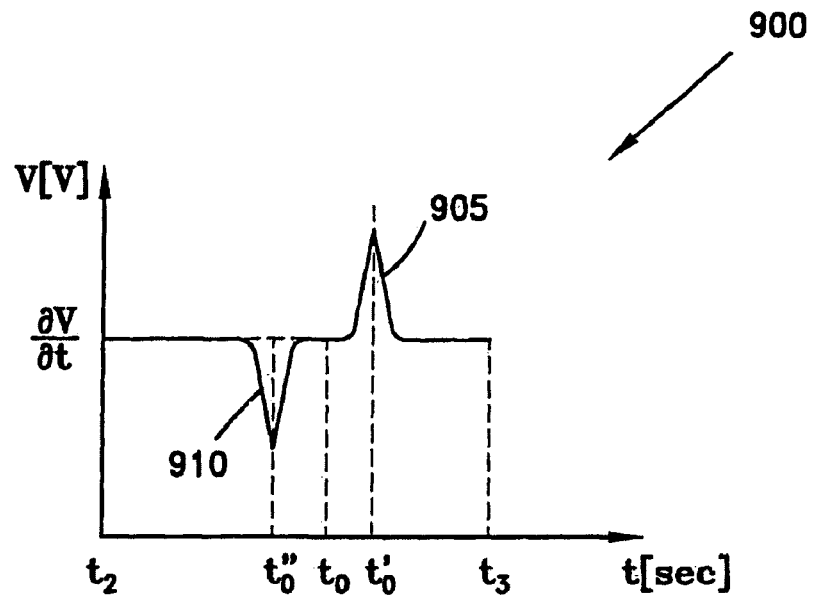
FIG. 6B is a schematic output voltage signal from a differentiator, while a system utilizing an apparatus of the present invention comprises a couple of the thermoelectric coolers, according to a preferred embodiment of the present invention.
Figure 6C:
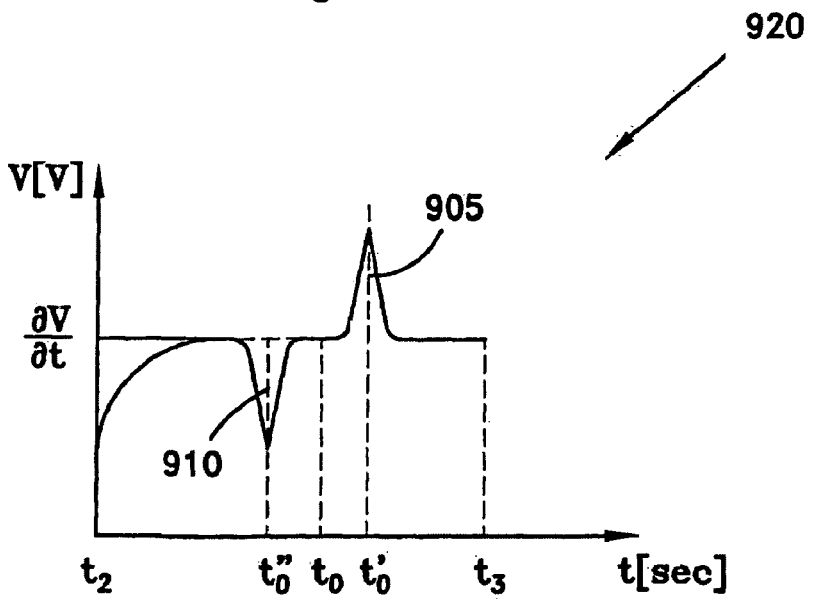
FIG. 6C is a schematic output voltage signal from a differentiator, while a system utilizing an apparatus of the present invention comprises a single thermoelectric cooler, according to another preferred embodiment of the present invention.

Pulse-generator 805 generates a series of current or voltage pulses, such as shown in FIG. 3A and FIG. 3E. These pulses are inputted to thermoelectric coolers 105 and 105'. In addition, signal 806 from said pulse-generator 805 activates timers 840, 840' and 840". Diodes 815 and 815' prevent signals 816 and 817 from being transferred back to pulse generator 808 or to timers 840, 840' and 840" at the time periods between the current or voltage pulses 201, 205 or 210 (FIG. 3A), etc. (for example, the time periods between $t_2$ and $t_3$, $t_4$ and $t_5$ (FIG. 3A)). Amplifier 820 amplifies signals 816 and 817 (outputted from thermoelectric coolers 105 and 105'), such as shown in FIG. 4C. Then differentiator 830 differentiates signal 821 (outputted from amplifier 820) in the time domain. The signal 831, as illustrated in FIG. 6B and FIG. 6C, comprises two spikes 905 and 910 obtained because of differentiating signal 641 or 541 shown in FIG. 4C and FIG. 5D, respectively. Analyzer 835 analyzes signal 831 and derives from said signal 831 the time marks of the time periods $t_0$, $t_0'$ and $t_0''$ (FIG. 5D). Then, analyzer 835 outputs signals 835, 836 and 837 (being the time marks of time periods $t_0$, $t_0'$ and $t_0''$) to the inputs of timers 840", 840 and 840', respectively. Said signals 835, 836 and 837 deactivate timers 840, 840' and 840" and terminate their time counting, said counting being initiated earlier by receipt of signal 806 from pulse-generator 805. In addition, signal 835 is inputted to the "Gate" of transistor 825, and it enables said transistor to transfer signal 821 (representing the amplified magnitude (value) $V_{t_0}$ of the thermoelectric coolers output signals 816 and 817) to pin 861 of microprocessor 860. Signal 821 is an amplified value of the pq value of extremum 642 (FIGS. 4C and 4D). Signals 850, 851 and 852 outputted from timers 840, 840' and 840", respectively and representing the time periods $t_0$, $t_0'$ and $t_0''$, are inputted to inputs 864, 863 and 862, respectively of microprocessor 860.

Microprocessor 860 processes signal 852 and obtains an average fluid velocity by using the following expression:

$$V_{AV} = \frac{d}{t_0 - \tau_B}$$

wherein d (FIG. 2) is the width of thermoelectric cooler 105'; and $\tau_B$ is determined empirically by taking a number of experiments. $\tau_B$ depends on the transfer time-constant of thermoelectric cooler 105', on the heat (thermal) capacity of heat-transfer surfaces 106, 106', 106" (FIG. 2), and on the heat (thermal) capacity of wall 102 (FIG. 2) of capillary tube 101. In addition, microprocessor 860 processes signals 822, 863 and 864, and it obtains a fluid temperature conductivity coefficient α by using the following expression:

$$\alpha = \beta_0 \cdot \frac{t_0' - t_0''}{V_{t_0}}$$

wherein $\beta_O$ is a proportionality coefficient depending on the fluid velocity in capillary tube 101; $V_{t_0}$ is a magnitude (value) of signal 822 inputted to pin 861 of microprocessor 860. $\beta_O$ is defined empirically by taking a number of experiments with different fluid flow velocities. If the value of α changes, then it means that the ingredients of the fluid within capillary tube 101 is also changing. The value of $V_{AV}$ and/or α and/or any other of the above parameters can be outputted to indicator 870. It should be noted, that indicator 870 can be a computer display or any other monitor.

A number of experiments were carried out, according to preferred embodiments of the present invention. In the experiments a system was used, which is similar to the system shown on scheme 800 (FIG. 6A). It should be noted, that the experimental set-up can comprise, for example, a capillary tube made from silicone (platinum) of "U-96410-13" model of the Cole-Parmer International company, located in USA. This capillary tube has an external diameter of 1 mm and an internal diameter of 0.5 mm.

In the said experiments, the flow of the fluid within the capillary tube was achieved by providing different fluid levels within said capillary tube, relatively to the horizontal axis. The average velocity $V_{AV}$ of the fluid microflow was determined by means of microprocessor 860 (FIG. 6A) by processing signal 852 (FIG. 6A). For validation of the experimental results and measuring the fluid microflow mass m' [mg/min], an analytical weight was used, having a tolerance of ±0.0001 [g]. The fluid flowing within the capillary tube was, in different experiments, distilled water and insulin (of various types). The capillary tube used in the experiments had a length of 0.5 m. In the experiments, the standard deviation (SD) between the fluid microflow mass m' [mg/min] determined by means of the analytical weight, and the fluid microflow mass determined by the system of the present invention, utilizing apparatus 500 (FIG. 5A) according to scheme 800 (FIG. 6A), was not greater than 0.02 with a repeatability of 0.995 for m' in the range of 0.2-100 [mg/min]. The internal diameter of the capillary tube can be, for example, 0.5 mm-5 mm. According to the present invention, the fluid can have any viscosity value. It should be noted that the strength of the narrow conduit, such as the capillary tube should be selected according to the pressure being activated on said narrow conduit. In addition, it should be noted that the fluid can comprise bubbles and particles of any form and size, which does not adversely influence the fluid microflow velocity measurements, according to the present invention. Of course, the size of the particles should be smaller than the diameter of the narrow conduit.

While some preferred embodiments of the invention have been described by way of illustration, it will be apparent that the invention can be practiced with many modifications, variations and adaptations, and with the use of numerous equivalents or alternative solutions that are within the scope of persons skilled in the art, without departing from the spirit of the invention or exceeding the scope of the claims.

The invention claimed is:

1. Apparatus for measuring a fluid microflow velocity within a capillary conduit, comprising:
   a. a capillary conduit through a wall of which a fluid is longitudinally flowable;
   b. at least one thermoelectric cooler mounted on, and in heat transfer relation with, said capillary conduit wall, each of said at least one thermoelectric coolers comprising:
      i. a plurality of Peltier thermal elements defining a common heating surface and a common cooling surface longitudinally spaced from said common heating surface; and
      ii. two conducting elements of a smaller radial dimension than said plurality of thermal elements, for thermally interfacing with said heating surface and said cooling surface, respectively, and with said capillary conduit wall, wherein said two conducting elements longitudinally and outwardly protrude from said heating surface and said cooling surface, respectively, so as to increase a heat transfer surface area between said at least one thermoelectric cooler and said capillary conduit wall and to increase the sensitivity of fluid velocity measurement;
   c. a voltage source for providing an input signal to said at least one thermoelectric cooler; and
   d. a processor for analyzing an output signal which is generated in response to said input signal and to a thermal reaction of said fluid to said at least one thermoelectric cooler, whereby to measure the velocity of said fluid.

2. Apparatus according to claim 1, comprising a first thermoelectric cooler and an additional thermoelectric cooler, said additional thermoelectric cooler being connected to said first thermoelectric cooler, or being located at a predetermined distance therefrom.

3. Apparatus according to claim 1, wherein each of the two conducting elements has at least one heat-transfer surface, being of a larger surface area than the plurality of thermal elements.

4. Apparatus according to claim 1, further comprising:
   a. a pulse generator for generating at least one current or voltage pulse and for providing said pulse to the electrical contacts of the at least one thermoelectric cooler;
   b. a differentiator for differentiating a thermoelectric cooler output signal;
   c. an analyzer for analyzing a signal outputted from said differentiator and for determining one or more time marks related to the fluid or gas temperature extremum, said extremum being created as a result of the corresponding current or voltage pulse provided by said pulse generator;
   d. at least one timer activated at the time of providing to said at least one thermoelectric cooler each current or voltage pulse, and deactivated at the time of receiving the time mark;
   e. a microprocessor for processing at least one time signal received from said at least one timer, and for determining a fluid or gas microflow velocity; and,
   f. an indicator or monitor for displaying said determined fluid microflow velocity or output means for providing a value corresponding to said determined fluid microflow velocity as an input to another device.

5. Apparatus according to claim 4, further comprising an amplifier for amplifying the thermoelectric cooler output signal.

6. Apparatus according to claim 4, further comprising at least one diode for preventing the thermoelectric cooler output signal from being transferred back to the pulse generator or to the at least one timer at a time period between each two current or voltage pulses.

7. Apparatus according to claim 4, further comprising a transistor for providing a magnitude of the thermoelectric cooler output signal to the microprocessor.

8. Apparatus according to claim 4, further comprising at least one analog-to-digital converter, for converting at least one analog signal and for inputting a converted signal to at least one input of the microprocessor.

9. Apparatus according to claim 4, wherein the microprocessor further determines whether one or more ingredients of the fluid flowing in the capillary conduit remain constant or are changed.

10. Apparatus according to claim 1, wherein the capillary conduit is a capillary tube.

11. A method for measuring a fluid microflow velocity within a capillary conduit, comprising:

e. providing a capillary conduit through a wall of which a fluid flows;
f. mounting at least one thermoelectric cooler on, and in heat transfer relation with, said capillary conduit wall, each of said at least one thermoelectric coolers comprising:
　i. a plurality of Peltier thermal elements defining a common heating surface and a common cooling surface longitudinally spaced from said common heating surface; and
　ii. two conducting elements of a smaller radial dimension than said plurality of thermal elements, for thermally interfacing with said heating surface and said cooling surface, respectively, and with said capillary conduit wall, wherein said two conducting elements longitudinally and outwardly protrude from said heating surface and said cooling surface, respectively, so as to increase a heat transfer surface area between said at least one thermoelectric cooler and said capillary conduit wall and to increase the sensitivity of fluid velocity measurement;
c. generating at least one current or voltage pulse by means of a pulse generator and providing said pulse to an electrical contacts of said at least one thermoelectric cooler;
d. differentiating a thermoelectric cooler output signal by means of a differentiator;
e. analyzing by means of an analyzer a signal outputted from said differentiator and determining one or more time marks related to the fluid temperature extremum, said extremum being created as a result of the corresponding current or voltage pulse provided by said pulse generator;
f. providing at least one timer activated at the time of providing to said at least one thermoelectric cooler each current or voltage pulse and deactivated at the time of receiving the time mark; and
g. processing by means of a microprocessor at least one time signal received from said at least one timer and determining by said microprocessor a fluid microflow velocity.

12. A method according to claim 11, comprising providing a first thermoelectric cooler and an additional thermoelectric cooler, said additional thermoelectric cooler being connected to said first thermoelectric cooler or being located at a predetermined distance therefrom.

13. A method according to claim 11, further comprising effecting heat-transfer to the capillary conduit by means of at least one heat-transfer surface, which has a larger surface area than heating or cooling surface area of the thermoelectric cooler.

14. A method according to claim 11, further comprising amplifying the thermoelectric cooler output signal by means of an amplifier.

15. A method according to claim 11, further comprising preventing, by means of at least one diode, the thermoelectric cooler output signal from being transferred back to the pulse generator or to the at least one timer at a time period between each two current or voltage pulses.

16. A method according to claim 11, further comprising providing to the microprocessor by means of a transistor a magnitude of the thermoelectric cooler output signal.

17. A method according to claim 11, further comprising converting by means of at least one analog to digital converter at least one analog signal and inputting a converted signal to at least one input of the microprocessor.

18. A method according to claim 11, further comprising determining by means of the microprocessor whether one or more components of the fluid flowing in the capillary conduit remain constant or are changed.

19. A method according to claim 11, wherein the capillary conduit is a capillary tube.

20. Apparatus for delivering a fluid according to claim 1, comprising a fluid-flow measuring element, or a fluid flow control element.

21. Apparatus according to claim 1, which is a drug-delivery apparatus.

22. Apparatus according to claim 21, which is an insulin pump.

23. Use of a device according to claim 1, as a fluid flow measuring or fluid flow controlling element in a fluid delivery apparatus.

24. Use according to claim 23, wherein the apparatus is a drug-delivery apparatus.

25. Use according to claim 24, wherein the apparatus is an insulin pump.

26. A method according to claim 11, further comprising displaying said determined fluid microflow velocity on an indicator or monitor or using a value representative of said determined velocity as the input to another device.

* * * * *